United States Patent [19]

Hirleman, Jr. et al.

[11] 4,188,121

[45] Feb. 12, 1980

[54] MULTIPLE RATIO SINGLE PARTICLE COUNTER

[76] Inventors: Edwin D. Hirleman, Jr., 432 E. Laquna, Tempe, Ariz. 85282; Sigmar L. K. Wittig, Hooverstrasse 27, D75 Karlsruhe 41, Fed. Rep. of Germany

[21] Appl. No.: 764,657

[22] Filed: Feb. 1, 1977

[51] Int. Cl.² ............................................ G01N 15/02
[52] U.S. Cl. .................................... 356/336; 356/343; 250/574
[58] Field of Search ............... 356/102, 103, 104, 336, 356/341, 342, 343; 250/574

[56] References Cited

U.S. PATENT DOCUMENTS

| 3,310,680 | 3/1967 | Hasegawa | 356/104 |
| 3,770,351 | 11/1973 | Wyatt | 356/104 |
| 3,835,315 | 9/1974 | Gravitt, Jr. | 250/574 |

*Primary Examiner*—Conrad J. Clark

[57] ABSTRACT

The present invention is an improved multiple ratio single particle counter. Intensities of scattered radiation are measured at more than two angles and ratios of these intensities are derived. These ratios are compared with calibration curves to determine an unambiguous measure of the particle parameter.

3 Claims, 5 Drawing Figures

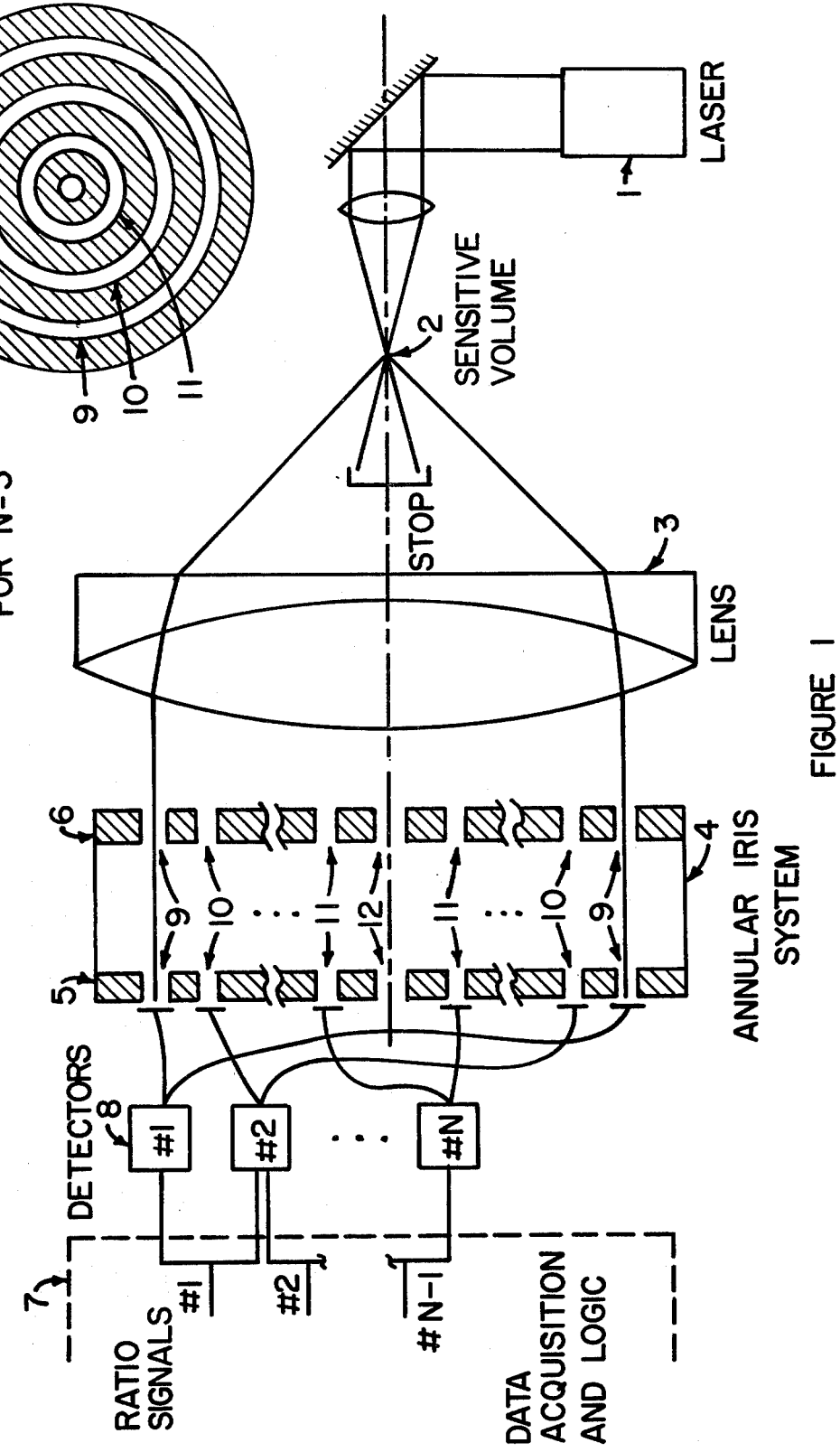

MULTIPLE RATIO SINGLE PARTICLE COUNTER

The present invention relates to an improved system for measuring one of the parameters of individual particles passing through a particle sampling zone and more particularly to improvements in the system disclosed in U.S. Pat. No. 3,835,315—Gravitt, issued Sept. 10, 1974.

In the system disclosed by Gravitt, laser or other light is focused to intensely illuminate a small region in space. This region, called the sensitive volume or particle sampling zone, is located in the field of light collecting apparatus which discriminates between the light scattered at two small angles and the light traveling in the light beam propagation direction. Detector means are used simultaneously to detect and record signals representing the intensities of the scattered light detected at the different angles. A measure of one of the parameters, i.e. the particle size, of a particle passing through the sampling zone is determined by measuring the ratio of the signals representing the intensities of the scattered light detected at two angles. This measurement is, however, non-unique or ambiguous since particles of different sizes may pass through the sampling zone and since many particle sizes can generate the same ratio signal.

It is an object of the present invention, therefore, to provide a new and improved system of the character described for measuring one of the parameters of individual particles passing through a particle sampling zone.

It is another and more specific object of the invention to provide a measuring system of the character indicated which obviates the disadvantages and short comings of the above described prior art systems.

It is still another object of the invention to provide an improved optical single particle counter which is capable of categorizing a particulate load in terms of concentration and size distribution.

In accordance with the present invention, these and other objects of the invention are achieved by obtaining two or more ratio signals derived from the measurement of the energies of bundles of light scattered by a given particle at three or more different angles and by comparing each ratio signal with a calibration standard to obtain a measure of the magnitude of the one parameter of the given particle. Apparatus is also provided for comparing the two or more measures of parameter magnitude thus obtained to determine whether they are the same or different and thus eliminate ambiguity in the interpretation of the particle parameter measurement.

The invention, both as to its organization and method of operation, together with further objects and advantages thereof, will best be understood by reference to the following description taken in connection with the accompanying drawings, in which:

FIG. 1 is a diagrammatic view in part illustrating one possible embodiment of the invention;

FIG. 2 is a sectional end view of the annular iris system embodied in the apparatus shown in FIG. 1;

In general, the objective of an optical single particle counter is to characterize a particulate load in terms of concentration and size distribution. Advanced optical systems for the particle parameter of size often use laser illumination of single particles and analysis of the scattered light characteristics to obtain information on the size and other physical parameters of a given particle. The sizes of many particles are measured and summed to determine an overall particulate size distribution. The use of lasers is advantageous due to the greater light intensity available as compared to conventional light sources, thereby allowing measurement of smaller particles and enhancing the ability for in-situ or non-interfering measurements. Arrangements using white light scattered in only one solid angle require an extremely well defined and compact sampling volume through which a representative sample of the particulate flow must be passed. Such prior art arrangements are typified by the available Royco and Bausch and Lomb commercial instruments and one such arrangement is disclosed by Friedman et al U.S. Pat. No. 3,705,711.

One problem with a laser system is the Gaussian intensity distribution in the beam, since single angle systems can not differentiate between a small particle passing through the high-intensity center of the beam and a larger particle passing through an off-center point of lower intensity. This problem can be eliminated by utilizing the ratio of light intensities scattered in two directions thereby cancelling the incident intensity effect as suggested by Hodkinson (App. Optics 5, 839, 1966) and Gravatt (U.S. Pat. No. 3,835,315, Sept. 10, 1974). This invention is a unique and independent improvement on the two-angle conventional ratio technique.

Description and Operation

Figure 3:
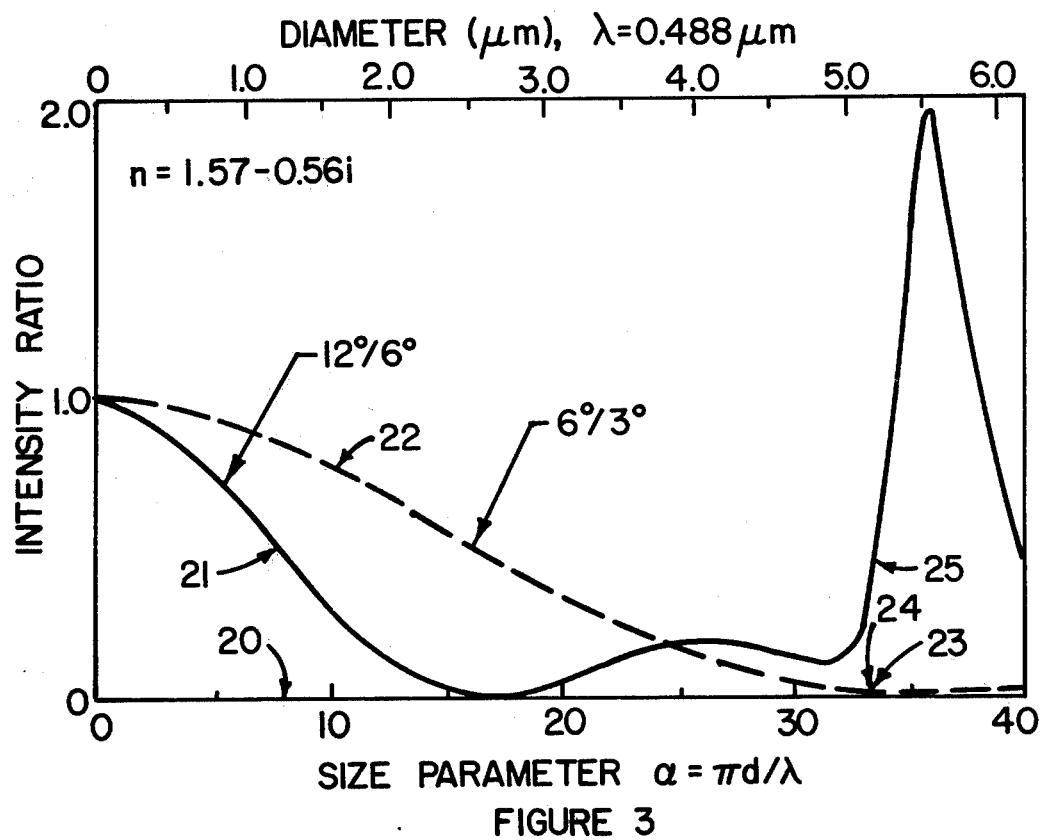
FIGS. 3 and 4 are sample calibration curves.

Referring now to the drawings and more particularly to FIG. 3 thereof, the dependence of scattering ratios as calculated from Mie theory for scattering of an electromagnetic wave by a sphere vs. particle size for an absorbing particle with index of refraction $n=1.57-0.56i$ is there shown. This plot is analagous to FIG. 2 of the Gravatt patent, although the curves in that patent ended as the ratio reached the first minimum vs. particle size (e.g. diameter $\approx 4.5$ $\mu$m for 10°/5° ratio from Gravatt). This invention is concerned with the effect of particles larger than the size where the first minimum occurs in a calibration curve. From FIG. 3 of the drawings it is apparent that particles larger than $\alpha \approx 17$ for the 12°/6° ratio would be "sized" incorrectly by the particle sizing instrument invented by Gravatt. For an assumed calibration curve as in FIG. 3 of the drawings a particle with $\alpha = 33$, point 23, would scatter a 12°/6° ratio equal to 0.5, point 25, and thereby be incorrectly classified as being of $\alpha \approx 7$, $\alpha$ level 20, corresponding to the same 12°/6° ratio of 0.5, point 21, within the applicable range of the two angle ratio counter ($0 \leq \alpha \leq 17$ for 12°/6° and $0 < \alpha \leq 25$ for 10°/5° from Gravatt).

The present invention involves the elimination of the aforementioned problem. The ratio of light scattered for at least one other pair of angles must be simultaneously analyzed for each particle passing through the sensitive volume or particle sampling zone. This second ratio then provides a consistency check on each particle analyzed. If the ratio measured at the second pair of angles corresponds to that predicted for the particle size within the valid range of the particular counter designed as indicated by the ratio measured at the primary pair of angles, then the particle can be counted. Otherwise the particle would be ignored as being of a size outside the range of the counter where particles could be accurately sized. For example from FIG. 3, the particle $\alpha = 33$, point 23, would scatter an intensity ratio of 0.03 point 24 at the 6°/3° pair, which would not agree with the value of 6°/3° ratio 0.8 point 22, as predicted for a particle of $\alpha=7$, $\alpha$ level 20, as determined from the 12°/6° ratio alone. Hence the consistency check would come up negative and the particle which would have been erroneously analyzed by a counter of the previous art (Gravatt, 1974) would be correctly discriminated and rejected by the multiple ratio concept of this invention.

(a) Extension to more angles

Figure 4:
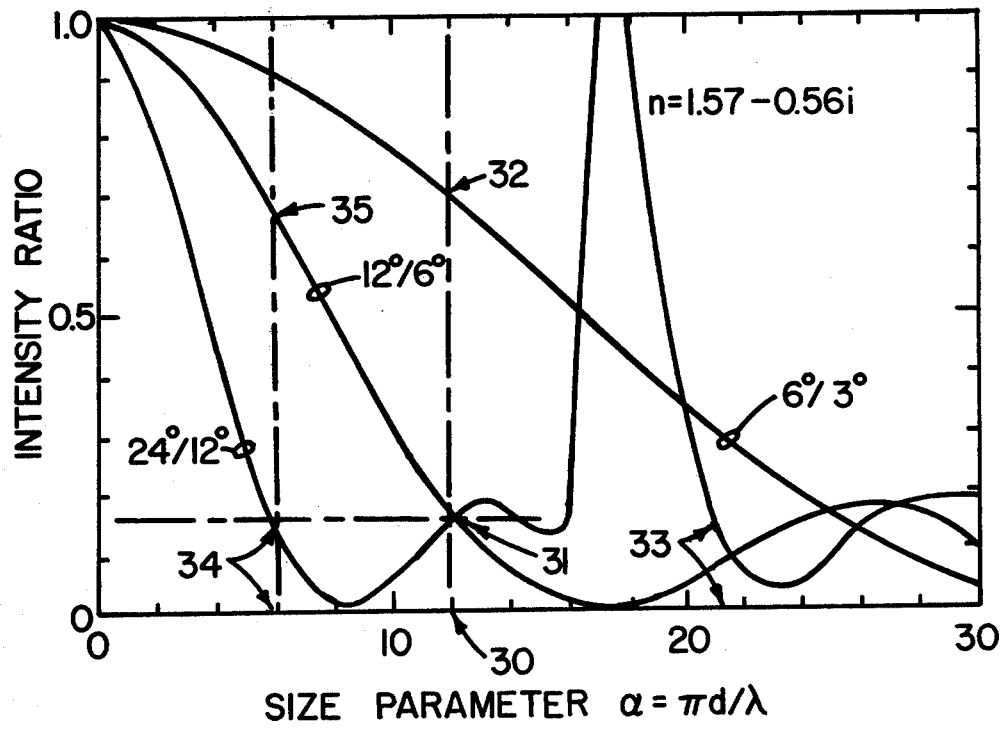

The multiple ratio concept allows the obvious extension to a larger number of angles than three thereby increasing the overall valid range of a particle counter utilizing this concept. In FIG. 4 of the drawings, there is indicated the predicted scattering characteristics for three pairs of angles. It is apparent that the valid range of a ratio counter shifts toward larger particle sizes as the angles approach the forward direction (0°). The extension of this invention to larger numbers of angles would utilize the following method. For maximum resolution, a particle should be sized using the ratio calibration curve for the largest pair of angles for which the consistency check is valid.

The n photodectors (n=2 for Gravitt) produce n signals 37 from each particle but with each signal being proportional to a light scattering property of the particle times the laser intensity incident on the particle. Denoting the n=1 signal as that from the photodetector at the largest scattering angle $\theta$ 36, ratios are taken of signals from photodetectors at adjacent scattering angles to give n−1 ratio signals 41 to be input to a logic section 42 of a multiple ratio instrument. The logic section 42 may be embodied as a hardwired or dedicated microprocessor or as software within a larger computer. A counting variable I is set equal to 1 43 and a first measure of particle size is obtained 44 using the first ratio signal from the n=1 and n=2 photodetectors and the corresponding calibration standard. The counter I is then incremented by 1 56 and another measure of the particle size is obtained if I=2 55 using a second ratio signal obtained by ratioing the signals from the n=2 and n=3 photodetectors and comparing with the corresponding calibration standard. After the second ratio signal is used to obtain a measure of particle size 53 the two measures of particle size are compared 50. If the two measures of particle size are equal to within some acceptable error band 51 the measure of particle size from the first ratio signal and corresponding calibration standard is output as a representative and accurate measure of particle size 52. If the two measures of particle size are not equal to within the acceptable error band the particle is then known to be larger than the upper sizing limit for the first ratio pair. In that case another measure of particle size is obtained using the third ratio signal 44 and that measure of particle size compared with the measure from the second ratio signal. If these second and third measures of particle size agree then the measure of particle size from the second ratio signal and corresponding calibration standard is output 52,57 as the most accurate representative measure of particle size.

The process of comparing two measures of particle size from two ratio signals continues until either agreement is found 51 or the last possible measures of particle size from the n−2 and n−1 ratio signals disagree 47. The measure of particle size determined from the n−1 ratio signal from the n−1 and n photodetector signals is ambiguous and uncertain since it can never be subjected to a consistency check. In the situation of disagreement between the n−2 and n−1 ratio signals 47 the particle is then outside of the valid range of the multiple ratio particle counter 48 and no unambiguous or representative measure of the size of that particle can be obtained.

For a specific example take n=4 with the n=1 photodetector at 24°, n=2 photodetector at 12°, n=3 photodetector at 6°, and n=4 photodetector at 3°. A particle of size parameter $\alpha=12$ 30 would give a first ratio signal at 24°/12° of 0.15 31 and the corresponding first measure of particle size would be $\alpha=6$ 34. The first size measure $\alpha=6$ is that size within the valid sizing range for 24°/12° ($0 \leq \alpha \leq 8$) corresponding to the measured ratio signal of 0.15 34. The second measure of particle size would be obtained from the second ratio signal from n=2 and n=3 photodetectors or 12°/6° ratio which would also be 0.15 31. However the measure of size determined from the 12°/6° ratio signal and the 12°/6° calibration curve standard would be $\alpha=12$ which is not within an acceptable error band (20%) of the $\alpha=6$ measured with 24°/12°. Thus the next ratio signal 6°/3° must be used to generate a third measure of particle size. The $\alpha=12$ particle would give a 6°/3° ratio signal of 0.7 32, and the measured ratio of 0.7 when compared with the 6°/3° calibration standard would obviously give $\alpha=12$ as the corresponding measure of particle size. The concidence check now between the two size measures $\alpha=12$ from 12°/6° and $\alpha=12$ from 6°/3° would agree to within experimental errors in the apparatus and thus the correct measure of particle size $\alpha=12$ would be output by the multiple ratio particle counter.

A particle of $\alpha=22$, points 33, would fail both consistency checks at 24°/12° and 12°/6° and thus could not be sized accurately by the four-angle system of FIG. 4. In short, there is accurate information subject to the consistency check on particle size available from n−2 ratios where n is the number of scattering angles monitored. Particles outside the "valid" range of a the present multiple ratio single particle counter system ($0 \leq \alpha \leq 17$ for FIG. 4 system) could be identified as such or sized only if there was a priori knowledge of a maximum expected particle size to be encountered.

In practice for particles of unknown index of refraction the calibration curves of FIGS. 3 and 4 are uncertain to near 20%, depending on the angle pairs. This uncertainty also has implications for the consistency check, in actuality a range of values for the checking ratio must be accepted for each measured value on the assumed ratio calibration curve. This range should be on the order of 20%.

Apparatus

The apparatus necessary to utilize this invention consists of simple and readily available components. The light source would be a laser 1 of any wavelength practical, although shorter light wavelengths would decrease the lower particle size limit of resolution. The sensitive volume would be defined by the light intensity distribution and the field of view of the collection optics. The laser beam could be focused on the sensitive volume if desired 2.

The collecting optics would serve to discriminate the light scattered at the various angles of interest. This task could be accomplished using a lens 3 to refract light scattered from the sensitive volume. The annular iris system 4 and lens determine the field of view. Light scattered to the detectors through the separate irises 9, 10 and 11 is detected and the ratios taken in the data acquisition section 7. Conventional detector and photomultiplier components may be used in constructing the present improved system.

The final portion of the present improved multiple ratio single particle counter system would be the data acquisition components. Any data acquisition system must accomplish the following tasks.
1. Valid signal discrimination—a technique to separate valid single particle signals from noise and particles not passing through the field of view of all of the angular detectors.
2. Ratio—a method to take the ratios of scattered light signals at pairs of angles.
3. Coincidence check—comparison of measured ratios with the calibrations curves calculated from Mie theory to determine that the particle is actually within the valid range of the counter.

Figure 5:
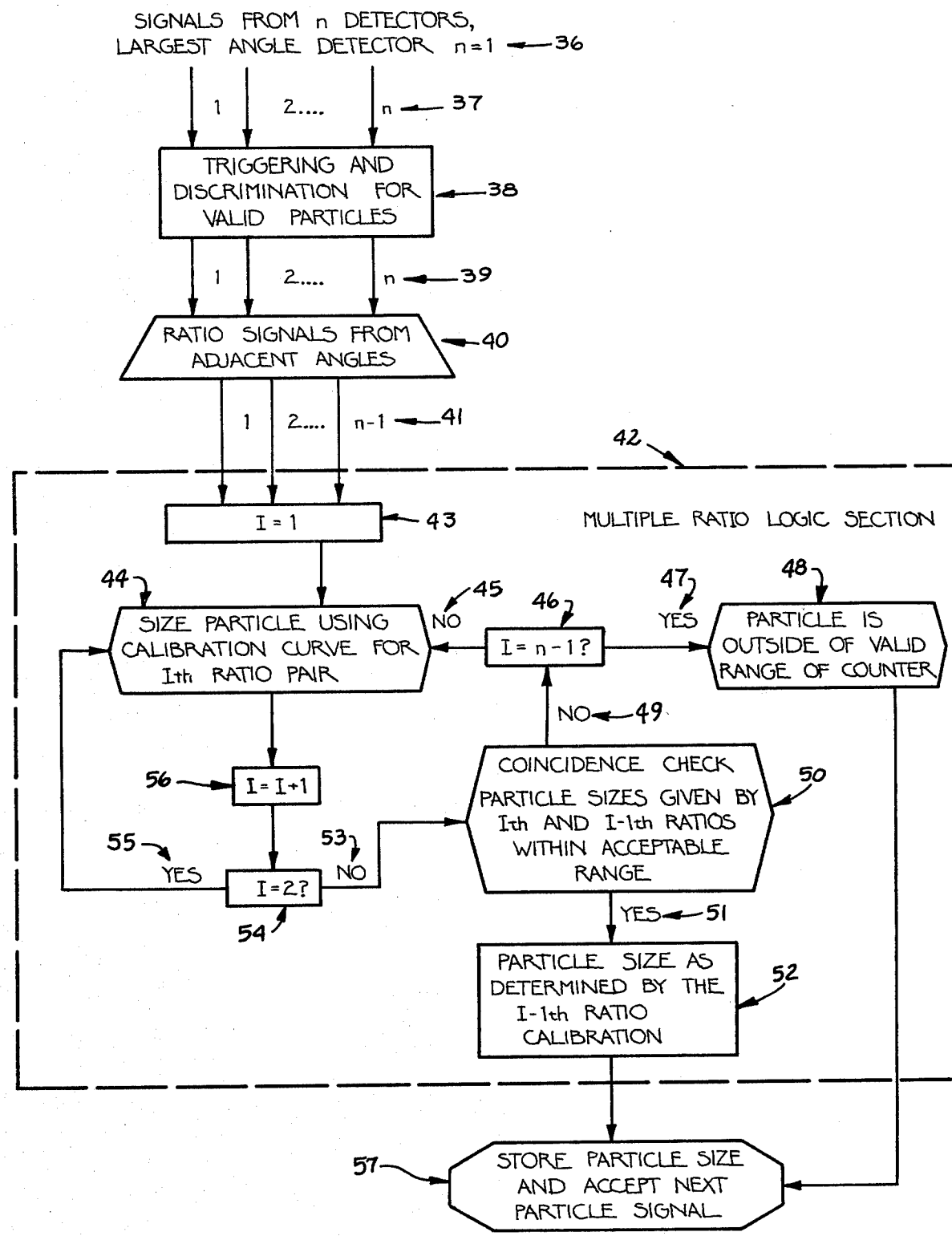
FIG. 5 is a logic flow chart illustrating the data acquisition and analysis system and concepts.

These steps are summarized in more detail in FIG. 5. As previously mentioned, the data acquisition could be accomplished in a number of ways, the major point of this invention is the concept. Preliminary tests by the inventor used an oscilloscope to record and discriminate the scattering signals and a digital computer program to perform the remaining data acquisition steps (2) and (3).

Advantages

The major advantage of this invention over the prior state-of-the-art concerns the ability to identify particles out size the valid range of a conventional ratio counter. Large particles would be sized incorrectly by the Gravatt (1974) invention, a problem which would be very significant during analysis of particulate matter of a highly polydisperse size distribution. The multiple ratio concept of this invention alleviates this critical problem.

What is claimed is:

1. A system for determining a parameter of a particle comprising:
   means for directing incident electromagnetic radiation to a particle under examination,
   means for detecting radiation scattered by said particle at more than two angles with respect to the direction of said incident electromagnetic radiation,
   means for determining at least two ratios of said signals,
   means responsive to said ratios for producing resultant signals representative of said parameter,
   means for comparing said resultant signals to determine an unambiguous measure of said parameter.

2. The system of claim 1 where said means for detecting radiation scattered by said particles simultaneously detects radiation at said more than two angles.

3. The system of claim 1, wherein said means for comparing said resultant signals operates to compare a resultant signal determined from radiation scattered at larger angles with a resultant signal determined from radiation scattered at the next smaller angles until the resultant signals are equal.

* * * * *